(12) United States Patent
Roberts

(10) Patent No.: US 9,226,940 B2
(45) Date of Patent: Jan. 5, 2016

(54) METHOD OF TREATING OCULAR DISORDERS

(71) Applicant: Kemin Industries, Inc., Des Moines, IA (US)

(72) Inventor: Richard Roberts, Johnston, IA (US)

(73) Assignee: Kemin Industries, Inc., Des Moines, IA (US)

(*) Notice: Subject to any disclaimer, the term of this patent is extended or adjusted under 35 U.S.C. 154(b) by 0 days.

(21) Appl. No.: 14/307,684

(22) Filed: Jun. 18, 2014

(65) Prior Publication Data

US 2014/0302169 A1    Oct. 9, 2014

Related U.S. Application Data

(62) Division of application No. 13/238,939, filed on Sep. 21, 2011, now Pat. No. 8,815,955.

(60) Provisional application No. 61/384,958, filed on Sep. 21, 2010.

(51) Int. Cl.

| | | |
|---|---|---|
| A61K 33/34 | (2006.01) |
| A61K 31/00 | (2006.01) |
| A61K 31/015 | (2006.01) |
| A61K 31/047 | (2006.01) |
| A61K 31/05 | (2006.01) |
| A61K 31/07 | (2006.01) |
| A61K 31/11 | (2006.01) |
| A61K 31/353 | (2006.01) |
| A61K 31/355 | (2006.01) |
| A61K 31/375 | (2006.01) |
| A61K 45/06 | (2006.01) |
| A61K 31/085 | (2006.01) |
| A61K 31/352 | (2006.01) |
| A61K 33/04 | (2006.01) |
| A61K 33/30 | (2006.01) |

(52) U.S. Cl.
CPC ............. *A61K 33/34* (2013.01); *A61K 31/00* (2013.01); *A61K 31/015* (2013.01); *A61K 31/047* (2013.01); *A61K 31/05* (2013.01); *A61K 31/07* (2013.01); *A61K 31/085* (2013.01); *A61K 31/11* (2013.01); *A61K 31/352* (2013.01); *A61K 31/353* (2013.01); *A61K 31/355* (2013.01); *A61K 31/375* (2013.01); *A61K 33/04* (2013.01); *A61K 33/30* (2013.01); *A61K 45/06* (2013.01)

(58) Field of Classification Search
IPC .................................. A61K 31/07,8/687, 8/347
See application file for complete search history.

(56) References Cited

U.S. PATENT DOCUMENTS

2007/0082064 A1    4/2007 Krawitz

OTHER PUBLICATIONS

Shaban et al., "A2E and blue light in the retina: the paradigm of age-related macular degeneration," Biological Chemistry 383(3-4):537-545, 2002.*

(Continued)

*Primary Examiner* — Rosanne Kosson
(74) *Attorney, Agent, or Firm* — Davis, Brown, Koehn, Shors & Roberts, P.C.; Kent A. Herink

(57) ABSTRACT

A method wherein subjects having or at risk for having hyperopia, presbyopia or astigmatism are administered a composition having an effective amount of ocular antioxidants, including specifically macular pigments, to prevent, treat, or delay the onset of age-related macular degeneration (AMD).

13 Claims, 4 Drawing Sheets

(56) References Cited

OTHER PUBLICATIONS

Areds, "A Randomized, Placebo-Controlled, Clinical Trial of High-Dose Supplementation With Vitamins C and E and Beta Carotene for Age-Related Cataract and Vision Loss", "Arch Opgthalmol", 2001, pp. 1439-1452, vol. 119, No. 9.

Barker, F. et al., "Nutritional Manipulation of Primate Retinas, V: Effects of Lutein, Zeaxanthin, and n-3 Fatty Acids on Retinal Sensitivity to Blue-Light-Induced Damage", "Invest Ophthalmol Vls Sci", 2011, pp. 3934-3942, vol. 52.

Bernstein, P. et al., "The value of measurement of macular carotenoid pigment optical densities and distributions in age-related macular degeneration and other retinal disorders.", "Vision Res", 2010, pp. 710-728, vol. 50.

Eye Disease Case-Control Study Group, "Risk factors for Neovascular Age-Related Macular Degeneration.", "Arch Ophthalml", 1992, pp. 1701-1708, vol. 110.

Gudmundsdorrir, E. et al., "With the rule astigmatism is not the rule in the elderly.", "Acta Opthalmol Scand", 2000, pp. 642-646, vol. 7.

Richer et al., "Double-masked, placebo-controlled, randomized trial of lutein and antioxidant supplementation in the intervention of atrophic age-related macular degeneration: the Veterans LAST study (Lutein Antioxidant Supplementation Trial).", 2004, pp. 216-230, vol. 75, No. 4.

Richer et al., "The Glare Hypothesis of Macular Pigment Function.", "Optom Vis Sci", 2008, pp. 858-864, vol. 84.

Seddon, J. et al., "Dietary Carotenoids, Vitamins A, C, and E, and Advanced Age-Related Macular Degeneration.", "JAMA", 1994, pp. 1413-1420, vol. 272.

Sharifzadeh, M. et al., "Nonmydriatic fluorescence-based quantitative imaging of human macular pigment distributions", "J Opt Soc Am A: Optics and Image Sci Vis", 2006, pp. 2373-2387, vol. 23.

Stringham, J. et al., "Macular Pigment and Visual Performance Under Glare Conditions.", "Optom Vis Sci", 2008, pp. 82-88, vol. 85.

Wang, J. et al., "Refractive Error and Age-Related Maculopathy: The Blue Mountains Eye Study.", "Invest Ophthalmol Vis Sci", 1998, pp. 2167-2171, vol. 39.

Wooten, B. et al., "Macular pigment: influences on visual acuity and visibility", "Prog Retinal and Eye Res.", 2002, pp. 225-240, vol. 21.

* cited by examiner

METHOD OF TREATING OCULAR DISORDERS

This application is a divisional application of U.S. patent application Ser. No. 13/238,939, filed on Sep. 21, 2011, which claims priority to U.S. patent application Ser. No. 61/384,958, filed Sep. 21, 2010, and incorporates the same herein in its entirety, by this reference.

BACKGROUND OF THE INVENTION

The present invention relates generally to a method of early diagnosis and treatment of ocular disorders and, more specifically, to the early diagnosis of subjects at risk for age-related macular degeneration and the administration of ocular antioxidants to subjects having hyperopia, presbyopia or astigmatism.

Hyperopia, presbyopia, and astigmatism are visual or ocular disorders that affect a significant percentage of the human population worldwide.

Age-related macular degeneration (AMD) is a disease associated with aging that gradually destroys sharp, central vision. The disease attacks the macula, the central area of the retina that allows a person to see fine detail. Individuals can lose all but the outermost peripheral vision, leaving dim images or black holes at the center of vision. AMD is a leading cause of vision loss and legal blindness in adults over 60 in the United States. An inverse relationship exists between the incidence of AMD and the amount of macular pigments, principally lutein and zeaxanthin, in the macula.

SUMMARY OF THE INVENTION

The present invention consists of the administration to subjects having or at risk for having hyperopia, presbyopia or astigmatism with a composition having a therapeutically effective amount of ocular antioxidants, including specifically macular pigments, to prevent, treat, or delay the onset of AMD. The invention also consists of a method for the early diagnosis of subjects at increased risk of developing AMD consisting of the existence or risk for the existence of hyperopia, presbyopia or astigmatism.

The composition may also include antioxidant compounds include vitamins A, C, E, and other vitamins exhibiting antioxidant activity; beta-carotene and other carotenoids including retinoids, retinal, retinaldehyde, and meso-zeaxanthin; zinc, copper, selenium and other minerals that may be cofactors of antioxidant enzymes or systems; natural extracts exhibiting antioxidant activity including but not limited to polyphenols, quercitin, anthocyanins, anthocyanidins, and the like; and synthetic antioxidants including BHT, BHA, BTHQ, or any synthetic analog of the natural antioxidants.

The supplementation can take any desired form, including addition of the composition to food, beverages, and/or dietary supplement tablets, capsules, and other more esoteric delivery forms. Furthermore, the composition including ocular antioxidants can take any form, including but not limited to powders, beadlets, crystals, liquids, dispersions, and the like as long as it can be delivered to the body in a form and in amounts that can be absorbed and used by the body

DETAILED DESCRIPTION OF PREFERRED EMBODIMENTS

Figure 1:
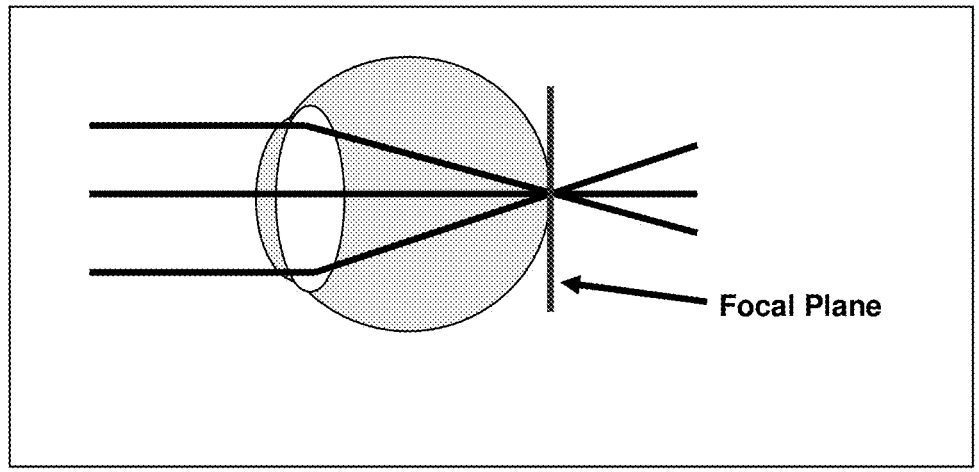
FIG. 1 is a graphical representation of the focal plane of visible light in a normal eye.

As used herein, the terms "age-related macular degeneration" and "AMD" refer to a disease associated with aging that gradually destroys sharp, central vision. The disease attacks the macula, the central area of the retina that allows a person to see fine detail.

"Macular pigment" refers to a composition that includes carotenoids found in the macula of the eye, principally lutein and zeaxanthin.

"Ocular antioxidant" includes (a) vitamins A, C, E, and other vitamins exhibiting antioxidant activity; (b) beta-carotene and other carotenoids including retinoids, retinal, retinaldehyde, and meso-zeaxanthin; (c) zinc, copper, selenium and other minerals that may be cofactors of antioxidant enzymes or systems; (d) natural extracts exhibiting antioxidant activity including but not limited to polyphenols, quercitin, anthocyanins, anthocyanidins, and the like; and (e) synthetic antioxidants including BHT, BHA, BTHQ, or any synthetic analog of the natural antioxidants.

As used herein, the term "therapeutically effective amount" refers to the amount/dose of a compound or pharmaceutical composition that is sufficient to produce an effective response (i.e., a biological or medical response of a tissue, system, animal or human sought by a researcher, medical doctor or other clinician) upon administration to a subject. The "therapeutically effective amount" will vary depending on inter alia the disease and its severity, and the age, weight, physical condition and responsiveness of the subject to be treated.

As used herein, the terms "treated" and "treating" refers to preventing or delaying the appearance of clinical symptoms of a disease or condition in a subject that may be afflicted with or predisposed to the disease or condition, but does not yet experience or display clinical or subclinical symptoms of the disease or condition. "Treating" also refers to inhibiting the disease or condition, i.e., arresting or reducing its development or at least one clinical or subclinical symptom thereof. "Treating" further refers to relieving the disease or condition, i.e., causing regression of the disease or condition or at least one of its clinical or subclinical symptoms. The benefit to a subject to be treated is either statistically significant or at least perceptible to the subject and/or the physician.

Hyperopia, or farsightedness, is a physical defect of the eye, primarily of genetic origin, in which the lateral axis of the eyeball (from cornea to posterior sclera) is too short or the lens of the eye exhibits insufficiently curvature for light to properly be focused upon the retina. This condition is normally easily detected through a routine eye examination and is readily corrected through the use of corrective lenses (surgery, glasses, or contact lenses).

Presbyopia, which is commonly confused with hyperopia, is an age-related visual disorder that affects virtually everyone to some extent. However, the degree of presbyopia varies between individuals. Although the exact cause of presbyopia is not known, it is generally accepted that it is a result of 1) a hardening of the lens of the eye and/or 2) an inability of the lens to adequately change curvature under the influence of the ciliary muscles and the zonules. The result is an improper focus of the image upon the retina. Regardless of the cause of presbyopia, at about the age of 40, most individuals begin to notice that nearby objects appear to be blurred. These individuals complain that their arms are not long enough to accurately focus upon nearby objects, especially when reading, particularly when trying to focus upon small print such as labels and/or newspapers, or when manipulating small objects with their hands. Therefore, the hallmark of presbyopia is that adults find it increasingly difficult to focus upon objects that are near to them. Distance vision is normally unaffected. Prebyopia is a slowly progressing ocular disorder. This progressive loss of near vision is slow enough that individuals may not complain about it for a considerable period of time. This is because of two reasons: 1) there is a stigma associated with wearing corrective lenses, especially glasses when they have never worn glasses and 2) when the distance between the eye and a blurry object is increased, the blurry object may come into better focus, especially in early presbyopia. In this early stage, presbyopia can be corrected to normal or near-normal vision through the use magnifying lenses (commonly referred to as reading glasses, which can be purchased at most drugstores). However, over the decades as we age, presbyopia normally becomes progressively worse thereby making vision correction by corrective lenses or surgery a necessity in many individuals.

Astigmatism is a defect of either the cornea (corneal astigmatism) or the lens (lenticular astigmatism) of the eye in which there is an irregular curvature to one or both of these structures. Corneal astigmatism is the most common type. In normal vision, the curvature of both the cornea and the lens are symmetrical along their horizontal and vertical planes creating a curvature similar to that of the surface of a basketball. Although irregular astigmatism (i.e., irregular curvatures in both the horizontal and vertical planes simultaneously, commonly referred to as compound astigmatism; or mismatched curvatures in both the cornea and lens) is known to exist, it is considered to be rare. In the typical form of astigmatism, the curvature in one of these planes (horizontal or vertical) is steeper than the curvature in the other plane. Therefore, the surface through which the light must pass in order to reach the retina resembles that of a football with the long axis directed either along either the horizontal or vertical axis of the eye. Since light passing through these mismatched curvatures cannot be focused equally, the focal point of light striking the retina in the two planes is not equivalent. When the light impinging upon the retina from one plane is in focus, light in the other plane is not in focus. This results in a blurring or smudging of the visual image. Although astigmatism less than about 0.5 diopters is not considered as needing correction, astigmatism greater than 0.5 diopter generally results in noticeable visual impairment and thereby requires correction. Further complicating this issue, although light passing through the normally curved plane of the cornea is focused properly, light in the astigmatic plane can be focused hyperopically (focused behind the retina) or myopically (focused in front of the retina) depending upon the curvature of the cornea.

At birth, the prevalence and degree of astigmatism is very high and primarily of corneal origin as it is in adults. Fortunately the incidence rate of astigmatism decreases as children grow as a result of a flattening of the astigmatic curvature of the cornea. In the age range of about 6 years and early adulthood, the incidence of astigmatism does not change appreciably. Approximately 5% of people in this age group exhibit astigmatism and about 75% of them exhibit "with the rule" astigmatism (i.e., the steepest slope of cornea is oriented along the vertical meridian). After the age of about 45, not only does the incidence of astigmatism increase, but additionally the direction of astigmatic corneal curvature also appears to change. Adult astigmatism, which has been estimated to reach an incidence rate of 35%, is primarily "against the rule" (i.e., exhibiting the steepest slope of the cornea along the horizontal meridian). This change in the orientation of the corneal slope is believed to be a result of a reduction in tension of the eyelids upon the eyeball that typically occurs with aging.

Relationship Between Ocular Defects, AMD, and Ocular Antioxidants

The relationship between hyperopia, presbyopia and astigmatism, Age-Related Macular Degeneration (AMD) and ocular antioxidants as described in this document, is based upon the known effects of the cornea and lens of the eye in relation to the focusing light of upon the retina; the available information on ocular disorders including AMD (the factors associated with their incidence; the effects of light upon the retina; and the reported effects of ocular antioxidants to reduce the potential damage induced in retinal tissues caused by that light, particularly the reported effect of ocular antioxidants in helping to reduce the progression of AMD). Although references have been found that tie some of these factors together as described in this document, no publications or references have been identified relating all of these factors in a unified manner. Therefore, some background is necessary to understand the relationship between these factors.

Multiple studies, particularly the Lutein Antioxidant Supplementation Trial (the LAST Study) conducted by Dr. Stuart Richer have produced results demonstrating that visual acuity, contrast sensitivity, and the amount of macular pigment in the human eye can be improved as a result of lutein and zeaxanthin supplementation or a combination of these xanthophylls with other antioxidants (Richer S, Stiles W, Statkute L, Pulido J, Frankowski J, Rudy D, Pei K, Tsipursky M, and Nyland J. (2004) Double-masked, placebo-controlled, randomized trial of lutein and antioxidant supplementation in the intervention of atrophic age-related macular degeneration: The Veterans LAST study (Lutein Antioxidant Supplementation Trial). *Optometry* 75:216-230). The LAST Study was conducted using a group of 90 patients with AMD over a time period of 12 months. The results show that the intake of xanthophylls with or without additional antioxidants increased visual parameters (visual acuity and contrast sensitivity) as well as helping retard progression of AMD in the test subjects. Even prior to the LAST study, the AREDS study (Age-Related Eye Disease Study Research Group. (2001) A Randomized, Placebo-Controlled, Clinical Trial of High-Dose Supplementation with Vitamins C and E and Beta Carotene for Age-Related Cataract and Vision Loss. AREDS Report No. 9. *Arch Ophthalmol.* 119:1439-1452) showed that the ingestion of a mixture of ocular antioxidants including vitamins A, C and E combined with beta-carotene, copper and zinc helps reduced the progression of AMD in subjects at risk for AMD or with early stages of this disease. Additionally, in a follow-up epidemiological analysis of data from the AREDS study, data gathered showed that the ingestion of lutein and zeaxanthin was related to a lower chance of progression of this ocular disease. Furthermore, the results of an epidemiological study conducted by Dr. Johanna Seddon at Harvard University (Seddon J, Ajani U, Sperduto R, Hiller R, Blair N, Burton T, Farber M, Gragoudas E, Haller J, Miller D, Yannuzzi L, and Willett W. (1994) Dietary carotenoids, vitamins A, C, and E, and advanced age-related macular degeneration. *JAMA* 272: 1413-1420) showed an inverse relationship between the incidence of AMD and the amounts of lutein and zeaxanthin ingested daily as part of the diet. These results along with a plethora of other results from in-vitro, ex-vivo, and animal and human studies support a definite relationship between the ingestion of ocular antioxidants and a reduction in the risk for the incidence and/or progression of AMD.

To understand the effects of antioxidants in the eye, it must be first understood that light entering the eye has potentially damaging effects upon the very ocular tissues that are responsible for vision. However, not all light impinged upon the eye enters the eye and not all wavelengths of light impinged upon the retina have potentially damaging effects. When light enters the human eye, the ultraviolet wavelengths are absorbed by the cornea and lens of the eye. This filtering of UV light effectively prohibits these potentially damaging wavelengths from reaching the retina. Upon passing through the lens, the visible wavelengths of light are focused upon the macular area of the retina. Of the wavelengths of visible light impinged upon the macula, the blue wavelengths are the shortest wavelength and exhibit the highest energy. Therefore, the blue wavelengths have the greatest potential to induce damage by absorption by photosensitizers and/or induction of free radicals. Although this theory of macular damage associated with the blue wavelengths of visible light has long been speculated, proof that these wavelengths actually damage retinal tissue has only recently been demonstrated in-vivo by Barker and coworkers (Barker F, Snodderly D, Johnson E, Shcalch W, Koepcke W, Gerss J, Neuringer M. (2011) Nutritional Manipulation of Primate Retinas, V: Effects of Lutein, Zeaxanthin, and n-3 Fatty Acids on Retinal Sensitivity to Blue-Light-Induced Damage. *Invest Ophthalmol Vis Sci.* 52:3934-3942).

Figure 2:
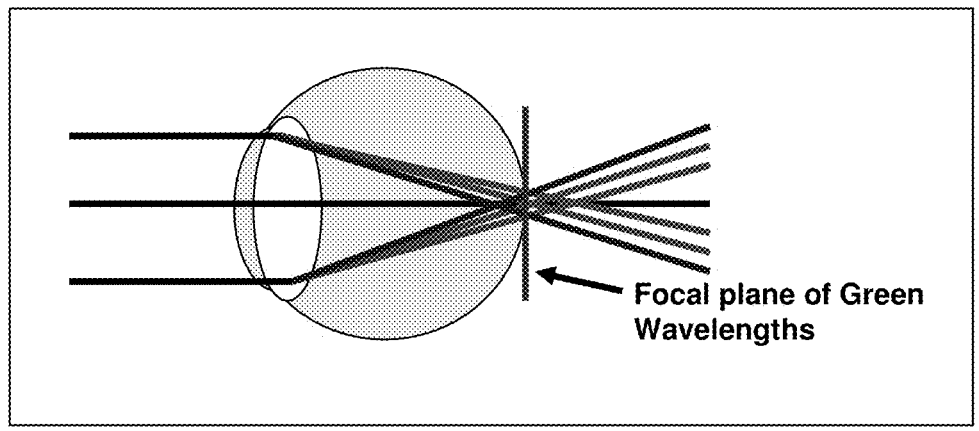
FIG. 2 is a graphical representation of focal plane for the chromatic wavelengths of visible light in the normal eye.

In a normal eye, the focal length of the lens (the distance from the lens to the focal plane of the retina) accurately matches the axial length of the eye as depicted in FIG. 1. In this focal process, the lens of the eye separates the wavebands of visible light in the same manner that a prism separates the wavelengths of light into its respective chromatic bands. Due to differences in the energy of these color bands, the lens is not able to focus each of these color bands at exactly the same distance. Therefore, the low energy red wavelengths are focused at the farthest distance from the lens and the high energy blue wavelengths are focused at the shortest distance from the lens. The green wavelengths are focused at an intermediate distance in comparison to the red and blue wavelengths. This chromatic separation of light is pictorially depicted in FIG. 2. Assuming perfect functionality of the cornea and lens as well as an eyeball of normal dimensions, the red wavelengths of light are focused behind the retina of the eye as just described. The green wavelengths of light are focused upon the focal plane of the retina. The blue wavelengths of light are focused in front (actually short) of the retina.

This distance-related color focusing issue is probably a result of natural selection since the blue wavelengths are the most energetic and damaging waveband of visible light striking the retina as described above. The presence of the macular pigment, which is composed of lutein and zeaxanthin, is critically positioned in the macular retina of the human (and the primate) eye in order to absorb these blue wavelengths of light. This absorption of the blue wavelengths of visible light helps reduce the potential damage that this waveband of light might have upon the sensitive cells comprising the macula. Additionally, a recent publication describes how the absorption of the blue wavelengths of visible light by the macular pigment helps reduce chromatic aberration, often referred to as the "blue haze" effect in human vision (Wooten B, and Hammond B. (2002) Macular pigment: influences on visual acuity and visibility. *Prog Retinal and Eye Res.* 21: 225-240).

Figure 3:
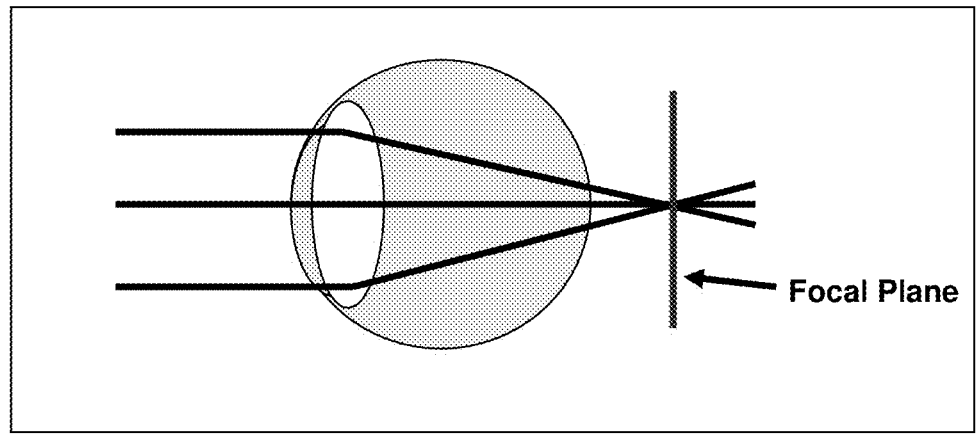
FIG. 3 is a graphical representation of focal plane for the visible light by the presbyopic/hyperopic eye.
Figure 4:
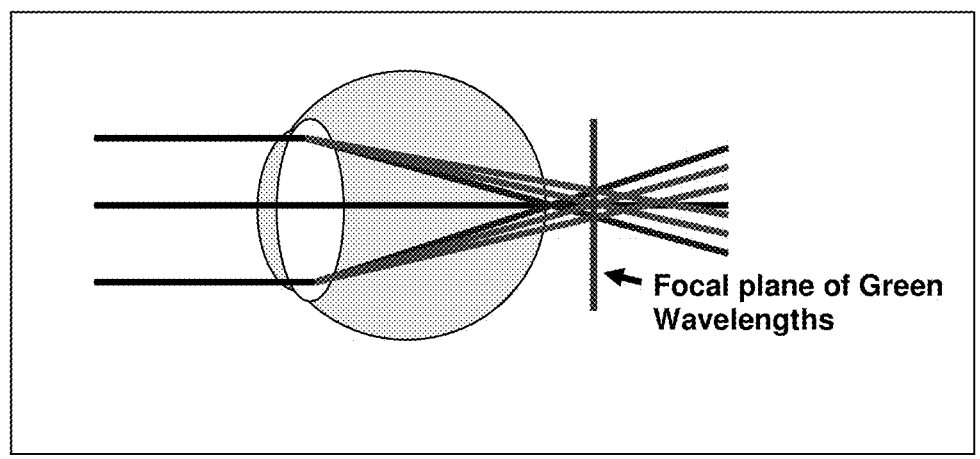
FIG. 4 is a graphical representation of focal plane for the chromatic wavelengths of visible light in the presbyopic eye.

The issues associated with the relationship between presbyopia and hyperopia, AMD, and antioxidants as these visual disorders as manifested in the human eye are that light focused by the lens no longer falls onto the retina as described above for the normal eye. Instead the light is focused further back on the retina. Therefore, in the presbyopic or hyperopic eye, the chromatic bands of visible light are focused at a further distance from the lens. This implies that the light is focused similarly to that shown in FIG. 3. This focal distance depends upon the degree of presbyopia/hyperopia. The greater the degree of presbyopia/hyperopia, the further behind the retina the light is focused.

Under presbyopic and hyperopic conditions, the chromatic separation of the wavelengths of visible light would cause the red and green wavelengths of light to be focused behind the retina and the blue wavelengths would be focused more close to or directly onto the retina. Focusing such potentially damaging light onto this sensitive retinal tissue will induce the generation of free radicals and reactive oxygen species in this tissue. These entities can cause considerable damage to the retinal cells in the macula, including damage to the photoreceptors and the retinal pigmented epithelium. Indeed, focusing increased amounts of the blue wavelengths of light upon these tissues, particularly over a period of time similar to that in which people notice the decreased ability to focus upon near objects caused by presbyopia, may initiate the cascade of damage that, over time, is known as AMD.

Despite broad acceptance among the ocular research community, macular pigment optical density (MPOD) is a relatively new concept amongst optometric and ophthalmologic communities that is gaining acceptance as a measure of the amounts of lutein and zeaxanthin in the macula of the living human eye as well as a marker of the health of the human eye. Healthy eyes contain higher levels of macular pigment thereby resulting in higher MPOD levels. This biomarker is being accepted because of the known properties of the macular pigment in absorbing the blue wavelengths of visible light, the antioxidant properties of constituents of the macular pigment, namely lutein and zeaxanthin, and the effects attributed to higher levels of macular pigment, namely reduction of chromatic aberration, increased glare tolerance/reduced glare recovery times, and better visual acuity (Richer, et al. 2004; Stringham J and Hammond B. (2007) The glare hypothesis of macular pigment function. *Optom Vis Sci.* 84: 858-864; Stringham J and Hammond B. (2008) Macular pigment and visual performance under glare conditions. *Optom Vis Sci.* 85: 82-88). Perhaps most importantly, it has been reported that approximately 46% of the population of the United States exhibits MPOD values that are in the low category (Stringham, et al., 2008). Furthermore, it is widely recognized that MPOD values decrease with age (Bernstein P, Delori F, Richer S, van Kuijk F, and Wenzel, A. (2010) The value of measurement of macular carotenoid pigment optical densities and distributions in age-related macular degeneration and other retinal disorders. *Vision Res* 50: 716-728). Therefore, the segment of the population with low MPOD values is believed to be more susceptible to damage induced by free radicals and reactive oxygen species in the macula caused by blue light exposure. Since such damage is suspected as being the basis upon which AMD develops, increasing MPOD values are being suggested as a way of reducing the risk for AMD while simultaneously reducing vision related issues, especially amongst people with AMD or at risk for this disease.

Hyperopia/Presbyopia and AMD

The epidemiological literature contains conflicting reports of a relationship between hyperopia and AMD with one report indicating that people who exhibit hyperopia are more likely to get AMD in later life (Hyman L, Lillenfeld A, Ferris F, and Fine S. (1983) Senile macular degeration: a case-control study. *Am J. Epidemiol.* 18:213-227) and other reports indicated that such a relationship was weak at best (Maltzman B, Mulvhill M, and Greenbaum A. (1979) Senile macular degeneration and risk factors: a case-control study. *Ann Ophthalmol.* 11: 1197-1201; Eye Disease Case-Control Study Group. (1992) Risk factors for neovascular age-related macular degeneration. *Arch Ophthalmol.* 110: 1701-1708; Sandberg, M, Tolentinl M, Miller S, Berson E, and Gaudio A. (1993) Hyperopia and neovascularization in age-related macular degeneration. *Ophthalmol.* 100: 1009-1013; Boker T, Fang T, and Steinmetz R. (1993) Refractive error and choroidal perfusion characteristics in potential with choroidal neovascularization and age-related macular degeneration. *Ger J. Ophthalmol.* 2:10-13; Wang J, Mitchell P, and Smith W. (1998) Refractive error and age-related maculopathy: the Blue Mountains Eye Study. *Invest Ophthalmol Vis Sci.* 39: 2167-2171). However, it must be noted that no clinical study has been conducted to confirm or refute the existence of such a relationship. Furthermore, no references have been found in the medical or scientific literature relating a potential increased incidence of AMD amongst individuals exhibiting presbyopia. However, data exists indicating that myopia (commonly referred to as nearsightedness) may indeed have the effect of helping to protect against AMD (Hirvela H, Luukinen H, Laara E, and Laatikainen L. (1996) Risk factors of age-related maculopathy in a population 70 years of age or older. *Ophthalmol.* 103: 871-877).

Although the reported protective relationship between myopia and protection against AMD can be easily rationalized based upon the fact that the blue wavelengths of light are focused at a significant distance in front of the retina in comparison to that of the normal eye, the link between hyperopia and an increased risk of AMD is somewhat more difficult to rationalize. Aside from people with very mild hyperopia, individuals who exhibit hyperopia are generally prescribed corrective lenses from an early age. Therefore, visual correction for hyperopia should limit the total amount of damage that might be induced in the retina by the blue light wavelengths impinging directly upon the retina. Therefore, unless the damage induced by the blue wavelengths of light in hyperopic individuals occurs very early in life (i.e., before the time of hyperopic correction) and such damage is dormant for many years (i.e., until the normal age of appearance of AMD which is accepted to be in the sixth to seventh decade of life), it is difficult to rationalize the link between normal hyperopia and AMD. There is always the chance the damage induced in undiagnosed childhood hyperopia is the link or at least an additional link between hyperopia and AMD. For this to be true, the damage induced by undiagnosed hyperopia would have to be undetectable for many years as just described. However, if this is the case, then this aspect of the relationship between hyperopia and AMD described in this work is considered to be covered by this document. However, in such an instance, there is a need for such individuals to be supplemented with ocular antioxidants across their entire life, not just in the mid- to later years of life. Despite that fact, ocular antioxidant supplementation in infants and children should still be considered to be important and advantageous to help reduce the possibility of AMD in later adulthood.

Additionally, there is always the possibility that damage induced by early childhood hyperopia and subsequently aggravated by presbyopia-induced damage is the actual link between the observed epidemiological relationship between hyperopia and AMD. Based upon the high metabolic activity exhibited by all cells of the human body in youth, it seems likely that any damage induced early in childhood should be readily repaired before the sixth decade of life. This should limit the importance of this link between childhood retinal light exposure, hyperopia, and AMD. Nonetheless, if this is the case, as stated above for the case of AMD resulting only from ocular damage induced by light upon the retina of the childhood hyperopic eye, supplementation of these individuals with ocular antioxidants throughout their lifetime should help reduce the incidence of AMD in late adulthood. This situation is considered to be covered within the relationships described in this document.

It is also possible that the relationship between hyperopia and AMD as described in the epidemiological literature is a result of presbyopia and not hyperopia. This is because it is virtually impossible to differentiate between these two ocular conditions upon a simple eye examination. Additionally, without a complete ocular history, an older person participating in an epidemiological study might not know the difference between these two conditions. Furthermore, no published studies in the epidemiological literature have provided any indication that they have questioned subjects about whether they have presbyopia as compared to hyperopia. Regardless, this issue is considered of little significance as it pertains to the relationship between ocular diseases and AMD since this document covers both hyperopia and presbyopia.

Returning to the original premise that presbyopia is the actual link between the damage observed in AMD, the age of onset of the potential damage caused by the presbyopic focus of blue light on the retina and the age of prevalence of ocular damage in AMD is logical. The prevalence of presbyopia increasing after the age of 40 and the age of diagnosis of AMD in the sixth to seventh decade allows a sufficient amount of time for the damage related to AMD to occur. Additionally, the effects of presbyopic changes upon the focal point of the damaging blue wavelengths of visible light upon the retina is consistent with the types of damage seen in AMD. Therefore, the initiation of dietary supplementation with ocular antioxidants at a much earlier age (in the early to mid-30s) than commonly undertaken in today's environment (in the mid- to late-50s) makes significant sense in order to help reduce AMD incidence in the elderly adult population. In fact, given the totality of the above potential links between early childhood damage caused by hyperopia and presbyopia in adulthood, it is probably most advisable to consider supplementation with ocular antioxidants throughout life, not just in later adulthood.

Astigmatism and AMD

Figure 5:
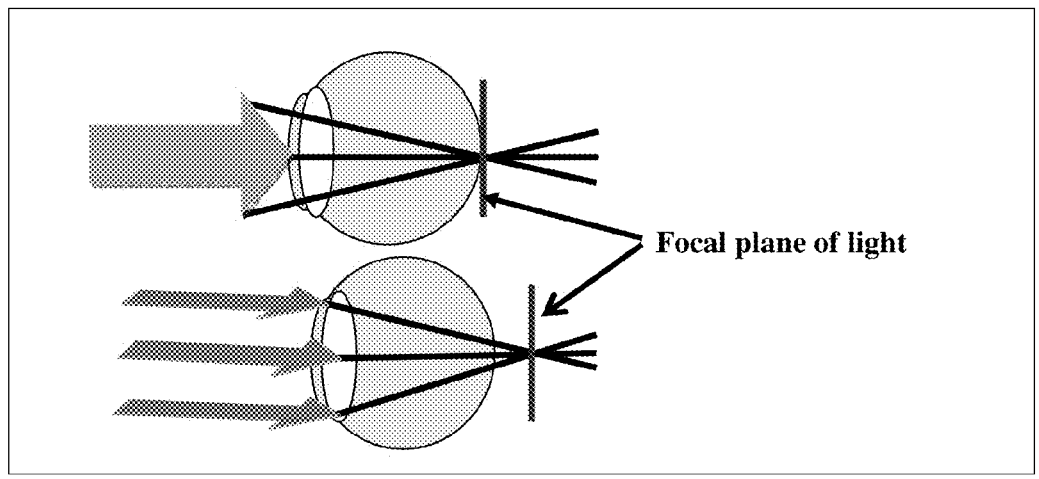
FIG. 5 is a graphical representation of the focal plane of light after passing through lens of a hyperopic, astigmatic eye; the two planes of light entering the eye in this figure are orthogonal (at 90°) to one another.

The principles described above regarding the focusing of light upon the macula of the eye in hyperopia and presbyopia equally apply in the circumstances where people suffer from astigmatism except for the fact that, in the astigmatic eye, light can be focused correctly in the normal orthogonal plane of the eye and improperly focused in the astigmatic plane as shown in FIG. 5 for a hyperopic astigmatic eye. In this example, light in the vertical plane is in focus at the retina whereas light in the horizontal plane is focus hyperopically (i.e., behind the plane of the retina). Similar to the case shown in FIG. 5, when the light entering the horizontal plane is separated prismatically into its component color wavebands, the blue wavelengths are focused directly upon the retina. These damaging blue wavelengths are capable of inducing significant damage upon the macular tissues which can result in AMD over the years as discussed previously. However, the damage noted may not encompass the entire macular area. Instead, because light in one plane is more focused upon the retina, the damage potential in presbyopics may be more to the central retina such as is found in choroidal neovascularization whereas the damage potential in astigmatics may be either more confined to the peripheral macular area such as found in geographic atrophy or more diffuse encompassing the central and peripheral retinal areas. This is not to imply that these two forms of AMD cannot be induced in either presbyopics or astigmatics but instead the focal properties of the eye exhibiting these conditions may be more likely to result in these forms of AMD.

As in the case of presbyopia, astigmatism increases with age and this condition is not readily noticed by people, particularly in the elderly, because astigmatism causes vision to be blurred or fuzzy but not completely out of focus (Gudmundsdorrir E, Jonasson F, Jonsson V, Stefansson E, Sasaki H, Sasaki K, and the Iceland-Japan Co-Working Group. (2000) "With the rule" astigmatism in not the rule in the elderly. *Acta Ophthalmol Scand.* 78:642-646). This finding implies that the need for correction for astigmatism can potentially exist for some time before it becomes serious enough to cause people to go their doctor to seek correction. The lag time between the existence of astigmatism and its correction means that the macula of the astigmatic eye is exposed to ever greater amounts of blue light exposure and potential damage.

Studies Demonstrating the Need for Macular Antioxidants in Presbyopia, Hyperopia, and Astigmatism As described above, the presence and relative amounts of the two principle antioxidants found in the macula, namely lutein and zeaxanthin, can be assessed by measurement of Macular Pigment Optical Density (MPOD). Additionally, as described above, it is known that MPOD declines with age which makes older people even more susceptible to AMD. Although MPOD values are a measure of only the amount of macular pigment (lutein and zeaxanthin) present in the eye, they are not the only antioxidants present in ocular tissues. However, because ocular antioxidants are derived from the same types of foods that macular pigment are obtained from, it is easy to hypothesize that people with low MPOD values also exhibit low levels of other ocular antioxidants. Such a hypothesis is also consistent with the published results (Bernstein, et al., 2010). Therefore, it is important to maintain high levels of macular pigment.

Figure 6:
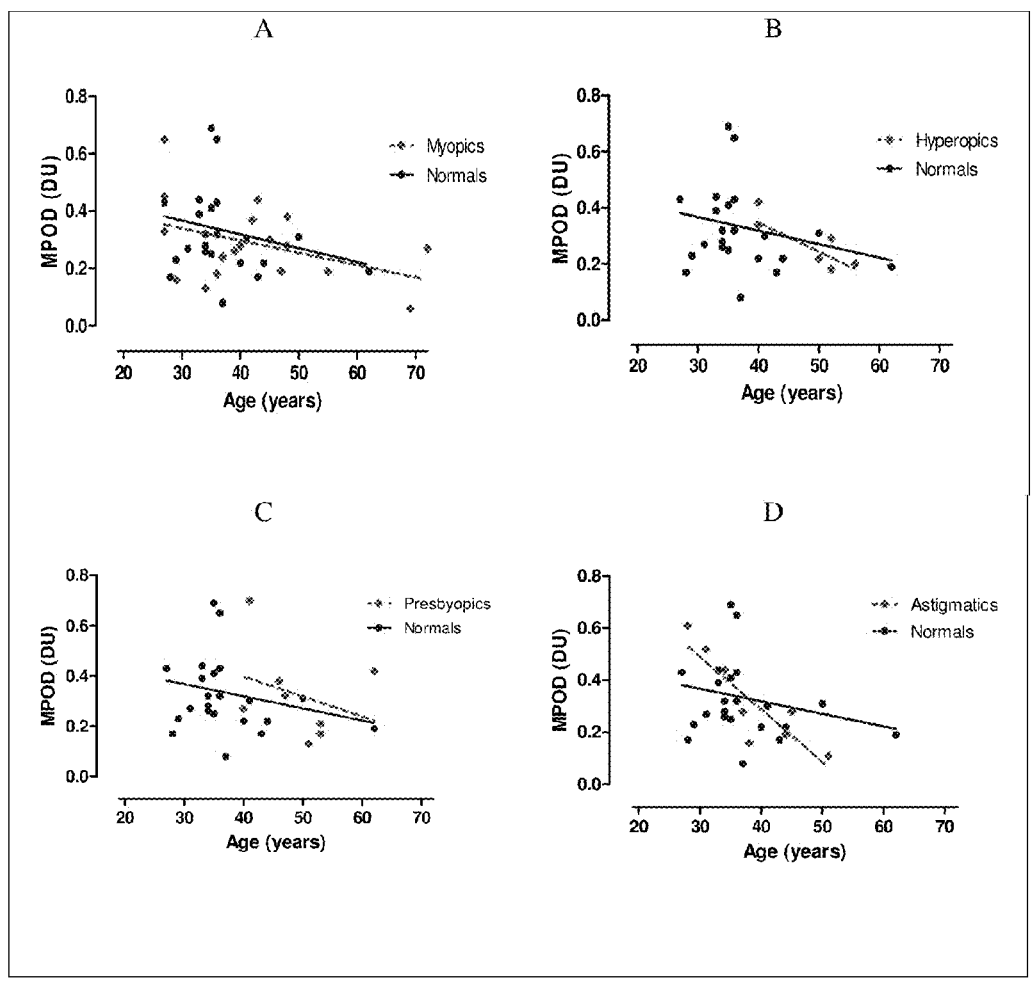
FIGS. 6A-D are graphical representations of MPOD values as a function of age for different types of vision correction in comparison to subjects who exhibiting vision that has never required correction (i.e., normals).

A study was conducted in which MPOD values were measured in a large, multi-ethnic population using an auto-fluorescence imaging instrument (Sharifzadeh M, Bernstein P, Gellermann W. (2006) Nonmydriatic fluorescence-based quantitative imaging of human macular pigment distributions. *J Opt Soc Am A: Optics and Image Sci Vis.* 23: 2373-2387). In total, 241 subjects volunteered for MPOD testing and values were obtained for 224 subjects. Of this total database, subjects were asked about their history of vision correction. Only subjects with and without a self-reported history of vision correction were included in the following analysis. Of the total number of subjects available, twenty-three indicated that their vision had never required any type of correction. These subjects were classified as the normal subject database. Eight subjects indicated that they had been diagnosed with only presbyopia, seven had been diagnosed with only hyperopia, nine had been diagnosed with only astigmatism, and an additional eighteen had been diagnosed with only myopia. The MPOD values were plotted as a function of subject age for the four types of visual disorders as shown in FIG. 6. FIG. 6A compares subjects with myopia to normals; 6B compares subjects with hyperopia with normals; 6C compares subjects with presbyopia to normals; and 6D compares subjects with astigmatism to normals.

As can be seen from the data in FIG. 6A, subjects with myopia do not show any appreciable difference in the rate of decline in MPOD as a function of age when compared to the rate of decline in MPOD with age in subjects who had vision that never required any correction. Similar comparisons of MPOD values with age in subjects who have had their vision corrected for hyperopia (FIG. 6B), presbyopia (FIG. 6C), or astigmatism (FIG. 6D) indicate a steeper decline in MPOD over the age range, especially subjects with astigmatic correction. Although a decline in MPOD values with age is not in itself an indicator of a predisposition for age-related macular degeneration, it definitely indicates an increased risk factor since studies have indicated that people with lower MPOD values are at greater risk for AMD (Bernstein, et al., 2010). Given the fact that presbyopia, and astigmatism are ocular conditions that occur with increasing frequency amongst people above the age of 40, this decline definitely indicates a need for supplementation with ocular antioxidants including lutein and zeaxanthin in people exhibiting these ocular disorders in order to reduce the potential damage to ocular tissues brought about by an increase exposure to blue light damage which could lead to AMD.

SUMMARY

The principles behind the relationships between MPOD values, blue light damage to ocular tissues, and the risk for AMD are based upon known data. They represent the cumulative blue light-induced damage from oxidative processes that occur in retinal tissues of the human eye that has been related to increased likelihood of AMD. Although the amount of cumulative damage required to elicit AMD is not known, it is known that ocular antioxidants are important in reducing the potential of such damage.

Based upon the data presented, eyes exhibiting hyperopia, presbyopia, and/or astigmatism exhibit a decline in MPOD values with age that is greater than in myopic eyes as well as eyes that have never required visual correction. This increased rate of decline in MPOD with age renders eyes with hyperopia, presbyopia, and/or astigmatism at greater risk for AMD. It is also possible that a combination of astigmatism with either hyperopia or presbyopia could result in an even higher risk of AMD than any one of the ocular conditions by itself. Therefore, such combination of ocular conditions are included in the present invention.

Supplementation of eyes with macular antioxidants, including but not limited to vitamins A, C, E, and other vitamins exhibiting antioxidant activity; beta-carotene and other carotenoids including lutein, zeaxanthin, retinoids, retinal, retinaldehyde, and meso-zeaxanthin; zinc, copper, selenium and other minerals that may be cofactors of antioxidant enzymes or systems, natural extracts exhibiting antioxidant activity including but not limited to polyphenols, quercetin, anthocyanins, anthocyanidins, etc.; and the synthetic antioxidants including BHT, BHA, BTHQ that increase ocular antioxidant levels will reduce the risk of blue light-induced damage to retinal tissues.

The cumulative damage theory of AMD is consistent with the onset of hyperopia or astigmatism regardless of age. Additionally, it is consistent with the onset of presbyopia, and adult onset astigmatism, both of which are reported to increase at about the age of 40. The slow progression of the ocular damage associated with AMD is consistent with rate of progression of presbyopia and/or adult-onset astigmatism. Such damage is probably compounded by the reluctance of people to wear any type of vision correction for presbyopia or astigmatism as well as the inability of people to take action on such visual changes until vision has deteriorated significantly.

The methods of the present invention are consistent with the knowledge that people with high levels of macular pigment are less likely to suffer from AMD. They are also consistent with the knowledge that MPOD levels decline with age, especially amongst people with hyperopia, presbyopic, and/or astigmatism. The presence of high levels of macular pigment may reduce the probability that people with hyperopia, presbyopia, and/or astigmatism would incur less blue light-induced retinal tissue damage than people with lower MPOD levels might incur. This is because the known blue light-absorbing capability and/or antioxidant capacity of the xanthophylls (lutein and zeaxanthin) comprising the macular pigment and the presence of other ocular antioxidants. These properties help limit the blue light-induced damage.

The methods of the present invention are not meant to cover damage that might be induced in the eye as a result of other ocular conditions/diseases that might also result in AMD, including but not limited to inherited conditions (a genetic component) or damage from other forms of retinopathies aside from AMD. Instead, the methods address the link between hyperopia, presbyopia, and/or astigmatism and AMD as well as the beneficial effect of ocular antioxidant supplementation upon reducing the risk associated with AMD. Supplementation with ocular antioxidants, as described above, is not limited to the xanthophylls that comprise the macular pigment. Ocular antioxidants as described above include vitamins A (1 to 150 IU/kg Body Weight (BW)/day), C (0.05 to 15 mg/kg BW/day), E (0.02 to 5 mg/kg BW/day), and other vitamins exhibiting antioxidant activity (0.01 to 500 mg/kg BW/day); lutein, zeaxanthin, beta-carotene and other carotenoids including retinoids, retinal, retinaldehyde, and meso-zeaxanthin (0.0001 to 2 mg/kg BW/day); zinc, copper, selenium and other minerals that may be cofactors of antioxidant enzymes or systems (0.0001 to 5 mg/kg BW/day), natural extracts exhibiting antioxidant activity including but not limited to polyphenols, quercitin, anthocyanins, anthocyanidins, etc. (0.001 to 75 mg/kg BW/day); and the synthetic antioxidants including BHT, BHA, BTHQ (0.001 to 15 mg/kg BW/day), or any synthetic analog of the natural antioxidants. Additionally, any combination of these ocular antioxidants may be used. The amounts described above pertain to a suggested dosage for an individual weighing approximately 150 pounds (approximately 70 kg). The relationships described are also not limited by the form of deliver of the above described materials and includes food, beverages, and/or dietary supplement tablets, capsules, and other more esoteric delivery forms. Furthermore, the ocular antioxidants can take any form, including but not limited to powders, beadlets, crystals, liquids, dispersions, and the like as long as it can be delivered to the body in a form and in amounts that can be absorbed and used by the body.

Even though the components and activity of the carotenoids comprising the macular pigment are described above in relation to reducing the potential damage associated with a relationship between hyperopia, presbyopia, and/or astigmatism and AMD, these relationships are not restricted to the activity of these xanthophylls. The relationships described also do not preclude the use of other antioxidants and associated molecules individually or in combinations that might reduce the oxidative damage associated with hyperopic-, presbyopic-, and/or astigmatic-induced AMD.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

What is claimed is:

1. A method of reducing the increased blue and ultraviolet light damage to the retina of a subject having a condition that causes such blue or ultraviolet light to fall disproportionally on or in front of the retina relative to the blue and ultraviolet light damage present in a subject having no such condition, wherein the condition is presbyopia or hyperopia or astigmatism, comprising administering to the subject having such condition a composition comprising a therapeutically effective amount of one or more ocular antioxidants.

2. The method of claim 1, wherein said ocular antioxidant is selected from the group consisting of antioxidant vitamins, carotenoids, antioxidant minerals, natural antioxidant extracts and synthetic antioxidants.

3. The method of claim 2, wherein said antioxidant vitamin is selected from the list consisting of vitamins A, C, and E.

4. The method of claim 2, wherein said carotenoid is selected from the list consisting of lutein, zeaxanthin, beta-carotene, retinoids, retinal, retinaldehyde, and meso-zeaxanthin.

5. The method of claim 2, wherein said antioxidant mineral is selected from the list consisting of zinc, copper, and selenium.

6. The method of claim 2, wherein said natural extract is selected from the list consisting of polyphenols, quercitin, anthocyanins, and anthocyanidins.

7. The method of claim 2, wherein said synthetic antioxidant is selected from the list consisting of BHT, BHA, and BTHQ.

8. The method of claim 2, wherein said therapeutically effective amount of said antioxidant vitamin is between 0.02 (1 IU) and 15 mg (150 IU) per kilogram of body weight of said subject per day.

9. The method of claim 2, wherein said therapeutically effective amount of said carotenoid is between 0.0001 and 2 mg per kilogram of body weight of said subject per day.

10. The method of claim 2, wherein said therapeutically effective amount of said antioxidant mineral is between 0.0001 and 5 mg per kilogram of body weight of said subject per day.

11. The method of claim 2, wherein said therapeutically effective amount of said synthetic antioxidant is between 0.001 and 15 mg per kilogram of body weight of said subject per day.

12. The method of claim 2, wherein said therapeutically effective amount of said natural extract is between 0.0001 and 20 mg per kilogram of body weight of said subject per day.

13. The method of claim 2, wherein said therapeutically effective amount of said synthetic antioxidant is between 0.0001 and 20 mg per kilogram of body weight of said subject per day.

* * * * *